United States Patent [19]

Dahms

[11] 4,124,470

[45] Nov. 7, 1978

[54] METHOD AND APPARATUS FOR ELECTROPHORESIS

[76] Inventor: Harald Dahms, 22 Lakeview Rd., Ossining, N.Y. 10562

[21] Appl. No.: 697,874

[22] Filed: Jun. 21, 1976

Related U.S. Application Data

[63] Continuation of Ser. No. 465,475, Apr. 30, 1974, abandoned.

[51] Int. Cl.$^2$ .................... G01N 27/26; G01N 33/16
[52] U.S. Cl. ..................... 204/180 R; 204/180 G; 204/299 R; 204/300 R; 204/301; 424/12
[58] Field of Search ........... 204/180 G, 180 S, 180 R, 204/299, 300, 301; 23/230 B; 424/12

[56] References Cited

U.S. PATENT DOCUMENTS

| Re. 27,552 | 1/1973 | Allington | 204/301 |
|---|---|---|---|
| 3,346,479 | 10/1967 | Natelson | 204/180 G X |
| 3,445,360 | 5/1969 | Via, Jr. | 204/180 G |
| 3,657,260 | 4/1972 | McLeester | 204/180 G X |
| 3,799,863 | 3/1974 | Zeineh | 204/180 G X |
| 3,855,111 | 12/1974 | Allington | 204/299 |
| 3,867,271 | 2/1975 | Hoefer | 204/180 G |

Primary Examiner—Arthur C. Prescott

[57] ABSTRACT

A method and apparatus for zone electrophoresis which is completely automatic and which requires no manual handling of the electrophoretic medium or the serum sample to be tested. In a preferred embodiment, prefabricated (empty) electrophoresis tubes are placed into a turntable. An automatic diluter then loads, in one operation, known amounts of sample serum and the electrophoretic medium into the tubes. Electrophoretic separation is then achieved automatically by application of a suitable voltage. The electrophoretic pattern produced in the tube is then measured by an optical probe which is dipped into the tube without disturbing the electrophoretic pattern established therein. This probe moves through the electrophoretic medium and measures the pattern quantitatively. This measurement can be directly transmitted to utilization equipment, such as data processing apparatus.

43 Claims, 9 Drawing Figures

FIG. 8
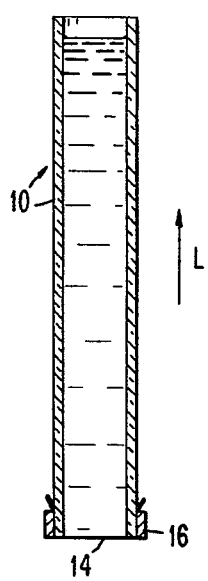
FIG. 9
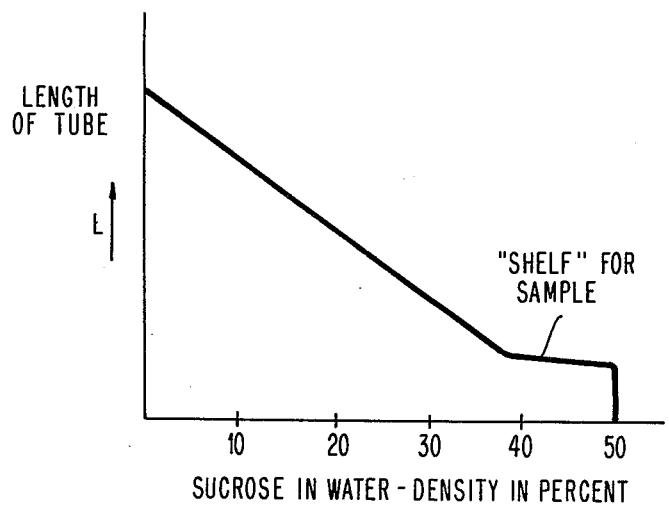
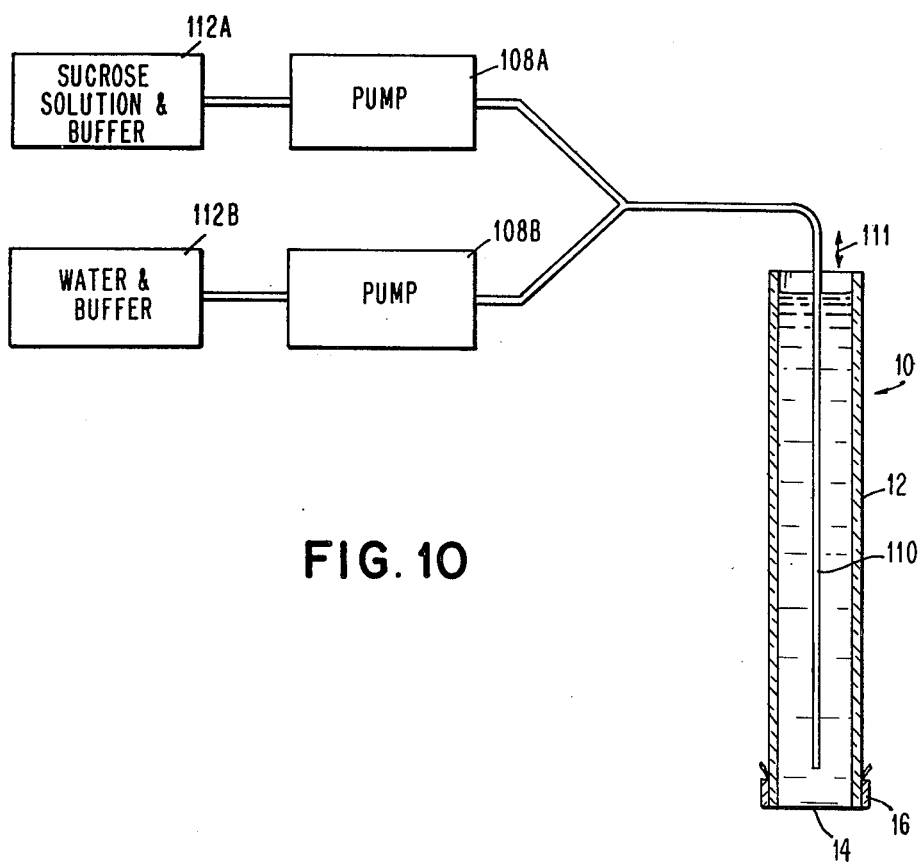
FIG. 10

METHOD AND APPARATUS FOR ELECTROPHORESIS

This is a continuation of application Ser. No. 465,475 filed Apr. 30, 1974, now abandoned.

BACKGROUND OF THE INVENTION

1. Field of the Invention

This invention relates to improved methods and apparatus for electrophoretic analysis of samples, and more particularly to an improved method and apparatus providing completely automatic electrophoretic analyses.

2. Description of the Prior Art

Electrophoretic analysis is a well known technique for identifying substances, which is particularly suited for clinical analysis of constituents in blood serum. The technique is based on the fact that most substances contain particles which, when subjected to an electric field, will disperse in an identifiable pattern.

The technique is used to separate organic and inorganic compounds of human, animal and inanimate origin. In particular, separation of the components of various body fluids is of considerable diagnostic use. By this technique, it is possible to identify abnormal protein in fluids such as blood and urine. Additionally, various types of hemoglobin and isoenzymes can be separated electrophoretically.

Although electrophoretic techniques have considerable promise in the areas of medicine and industrial activity, present laboratory electrophoresis involves a number of manual steps which require a technician's time and which give rise to numerous errors and inaccuracies. These prior art electrophoretic techniques are illustratively described in U.S. Pat. No. 3,421,998. In that patent, electrophoretic separation involves the following steps:

1. An electrophoresis strip (porous strip) is saturated with a buffer solution and then placed in an electrophoresis chamber where it is fastened.
2. The serum sample to be tested is applied by a technician using a special sample applicator. The amount of sample applied is so small (about 1 microliter) that it is not quantitatively known so that the resulting determinations are of relative percentages of the protein fractions rather than absolute values.
3. Electrophoresis is then performed by applying a DC voltage for a period of time.
4. The electrophoresis strip is taken out of the chamber and treated in dye solutions, rinsing solutions and cleaning solutions by the technician.
5. The strip is then dried and the electrophoretic pattern is measured in an optical densitometer.

Thus, it is readily apparent that steps 1,2,4 and 5 involve a considerable number of manual operations. However, apparatus based on these operational steps is presently being extensively marketed.

Another type of electrophoresis operation is described in U.S. Pat. No. 3,432,414. In this reference, the analytical procedure consists of the following steps:

1. A liquid electrophoresis medium containing pH buffer and agarose is put into an electrophoretic vessel by a technician. This operation forms a thin layer on the top of a quartz plate which is transparent to UV radiation.
2. Each serum sample to be tested is brought into contact with a special sample applicator, as described in U.S. Pat. No. 3,360,454. The applicator is then brought into contact with the layer of electrophoretic medium. Here again, the amount of serum applied is not quantitatively known, hence the determination yields only relative percentages of fractions present in the serum.
3. After electrophoresis and quantization, the technician has to clear the electrophoretic chamber manually.

Again, this method of electrophoresis requires numerous manual steps which are time consuming and which lead to inaccuracies.

Other methods of electrophoresis are known which are not as widely used for clinical serum analysis. These other methods use columns such as are described in U.S. Pat. No. 3,384,564. However, this latter type of electrophoresis also involves several manual steps, as for instance:

1. The column is filled manually with gel, and the gel is then polymerized.
2. The sample to be tested is applied manually onto the gel in the column.
3. A buffer solution is added on top of the serum sample and electrophoresis is then carried out by the application of a voltage to the sample.
4. The gel column is then dyed and quantitatively measured. This procedure usually takes hours because the thick gel columns require a long time for dye diffusion to occur.

Thus, it is readily apparent that the prior art does not suggest an electrophoretic method or apparatus which can automatically yield determinations of absolute amounts of electrophoretic fractions. Further, the prior art does not teach or suggest an apparatus or method which is automatic or which can be automated in order to require only a minimum of operator time. In contrast, the present invention requires no manual handling of the electrophoretic medium or the sample to be analyzed, at any time during the analysis operation.

It will be appreciated that the manual operations described above are never performed at exactly the same time in the procedure. For example, the time between applying the sample and the start of the electrophoresis, or the time between the electrophoresis and the scanning of the developed pattern will vary slightly from one sample analysis to the next when manual steps are involved. This, in turn, affects the accuracy and reproducibility of results.

Accordingly, it is a primary object of this invention to provide completely automatic zone electrophoretic analysis.

It is another object of this invention to provide electrophoretic analysis which requires no manual steps and which utilizes improved apparatus in order to yield precision results quickly.

It is still another object of this invention to provide an electrophoretic technique for analysis of samples in which all steps of the technique are achieved with constant, reproducible timing for each sample which is analyzed.

It is still another object to provide an improved technique for electrophoretic analysis which reduces costs.

It is a further object of this invention to provide automatic electrophoresis with apparatus for improved scanning of electrophoretic patterns.

It is another object of this invention to provide an electrophoretic technique using an improved apparatus and method for loading sample serum for testing.

It is a still further object of this invention to provide improved electrophoretic techniques for determining isoenzymes.

BRIEF SUMMARY OF THE INVENTION

This improved zone electrophoretic apparatus and method utilizes loading of electrophoretic tubes onto a conveyor, such as a turntable, and then automatically filling the tubes with electrophoretic medium and the sample to be tested. After this, electrophoretic separation is carried out automatically. The electrophoretic pattern established by application of a voltage is then measured automatically and the results transmitted to utilization equipment, such as a computer.

Broadly, the apparatus used for automatic operation comprises a conveyor means, such as a turntable, and numerous electrophoretic vessels, such as tubes. Conveniently, these tubes have closures at one end thereof which can conduct electrolytic current, and also have a conductive means at the other end. The tubes are loaded with the electrophoretic medium and the sample to be tested by an automatic diluter which, in one operation, will load known amounts of sample and electrophoretic medium into the tubes. When a voltage is applied between the conductive means and the closure, an electrophoretic pattern is produced in the tubes. The conveyor (turntable) then transports the vessels from the loading stations to a scanning station while the electrophoretic separation is proceeding.

Measurement of the electrophoretic patterns is achieved by a new type of optical probe which is dipped into the electrophoretic tube without disturbing the pattern established therein. This probe travels vertically through the electrophoretic medium (i.e., in a direction to scan the pattern) and measures the pattern quantitatively.

Isoenzymes are determined by dispensing a reagent into the tubes after electrophoresis occurs, using a dispensing means which moves along an axis of the tube while the reagent is being dispensed. Again, the vessel is automatically transported from the reagent dispension station to a scanning station while the reaction is proceeding.

Thus, it is apparent that the present invention provides a means and technique which satisfies the ever increasing demand for laboratory automation in order to be able to analyze more samples in less time with increased accuracy and precision. In turn, this reduces the cost of analysis and is particularly important in the area of health care, where high costs are an ever increasing problem.

These and other objects, features, and advantages will be more apparent from the following more particular description of the preferred embodiments.

BRIEF DESCRIPTION OF THE DRAWINGS

FIGS. 8–10 are used to illustrate density gradient electrophoresis as can be performed automatically using the present techniques. In particular, FIG. 8 shows the presence of a density gradient in the electrophoresis tube of FIG. 1, while FIG. 9 shows a plot of the distribution of the varying density of the solution in the electrophoresis tube.

FIG. 10 is a schematic illustration of apparatus for the preparation of density gradients in an electrophoretic vessel, such as that shown in FIG. 1.

DETAILED DESCRIPTION OF THE PREFERRED EMBODIMENTS

Figure 1:
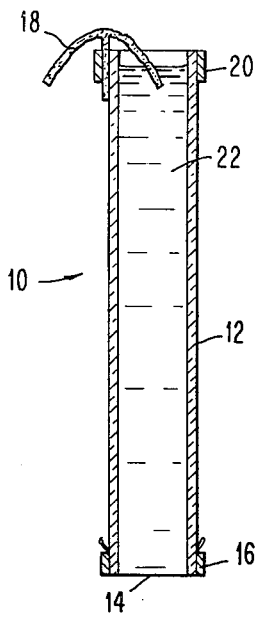
FIG. 1 shows a disposable electrophoresis vessel particularly suited for automatic electrophoresis operations.

FIG. 1 shows a disposable electrophoretic vessel 10 in which the electrophoretic pattern can be established. In this embodiment, vessel 10 is comprised of the tube 12, which is preferably cylindrical, and which is made from materials such as inert plastic or glass. The shape of the electrophoretic vessel is arbitrary, and can be adpated to the system in which it is used. For instance, tubular vessels are particularly suitable for use in turntables. The bottom of tube 12 is closed with a membrane 14 which is in turn held taut by rubber ring 16. Membrane 14 typically is comprised of a material such as cellophane. A suitable example is the dialysis membrane (type C) sold by the Technicon Corporation, Tarrytown, N.Y. In operation, membrane 14 conducts electrical current and keeps the electrophoretic medium in vessel 10. Cellophane is a material which will conduct electrical current when wetted with the electrophoretic medium which contains an electrolyte. Other materials, while less preferable, may also be used if they satisfy these requirements.

The upper end of tube 12 is provided with wick 18 which is held by elastic ring 20. Wick 18 is, for example, made of absorbent filter paper or any other material which can absorb liquid by capillary action. Wick 18 will conduct electrical current when saturated with electrolyte solution. The use of such wicks is well known in the electrophoretic art.

Electrophoresis vessel 10 is preferably delivered in an unfilled form to the clinical laboratory where it will be used. Later, during automatic operation of the electrophoresis apparatus, an electrophoretic medium 22 will be placed in the vessel 10.

This medium is preferably a liquid buffered aqueous solution. It is generally preferred to use aqueous solutions with increased viscosity as compared to plain aqueous solutions; however, plain aqueous solutions may also be used. A preferred solution having suitable viscosity contains, for example, the composition comprising 0.15 Vol.% Agarose, 0.23 Vol.% Dextrin, 0.7 g. $NaH_2PO_4$ per 100 ml., with the pH adjusted to pH 8.6. This solution has been described by K. H. Fuss in Zeitschraft fuer Analytische Chemie, Vol. 243, page 512.

The electrophoretic composition is not critical and other electrophoretic media can also be used. For example, reference is made to an article by N. Ressler and S. D. Jacobson which appeared in the Journal of Laboratory and Clinical Medicine, July, 1959, page 115. The electrophoretic medium described therein contained 0.05 moles of tris-hydroxymethyl aminoethane and 0.5 moles of LiCl per liter, adjusted to pH 8.6 with HCl.

It has been mentioned that liquid buffered solutions are preferable for the electrophoretic medium 22. However, gels which do not flow freely at room temperature may also be used. Such gels may contain agarose at concentrations between 0.2 and 1 Vol.% to be "solid". However, liquid gels are preferred and these usually contain agarose in an amount below 0.2 Vol.%. Also, the electrophoretic medium may be liquid at higher temperatures while it is a gel at lower temperatures. In this situation, vessel 10 may be filled at a higher temperature (liquid medium) and then allowed to cool to a lower temperature, so that the medium will gel. After this, electrophoresis is performed.

The tubular electrophoresis vessel 10 may be typically 15 mm. in diameter and 90 mm. long. The volume of serum sample may be typically 30 microliters while the volume of the electrophoretic medium is then 14 milliliters.

Figure 2:
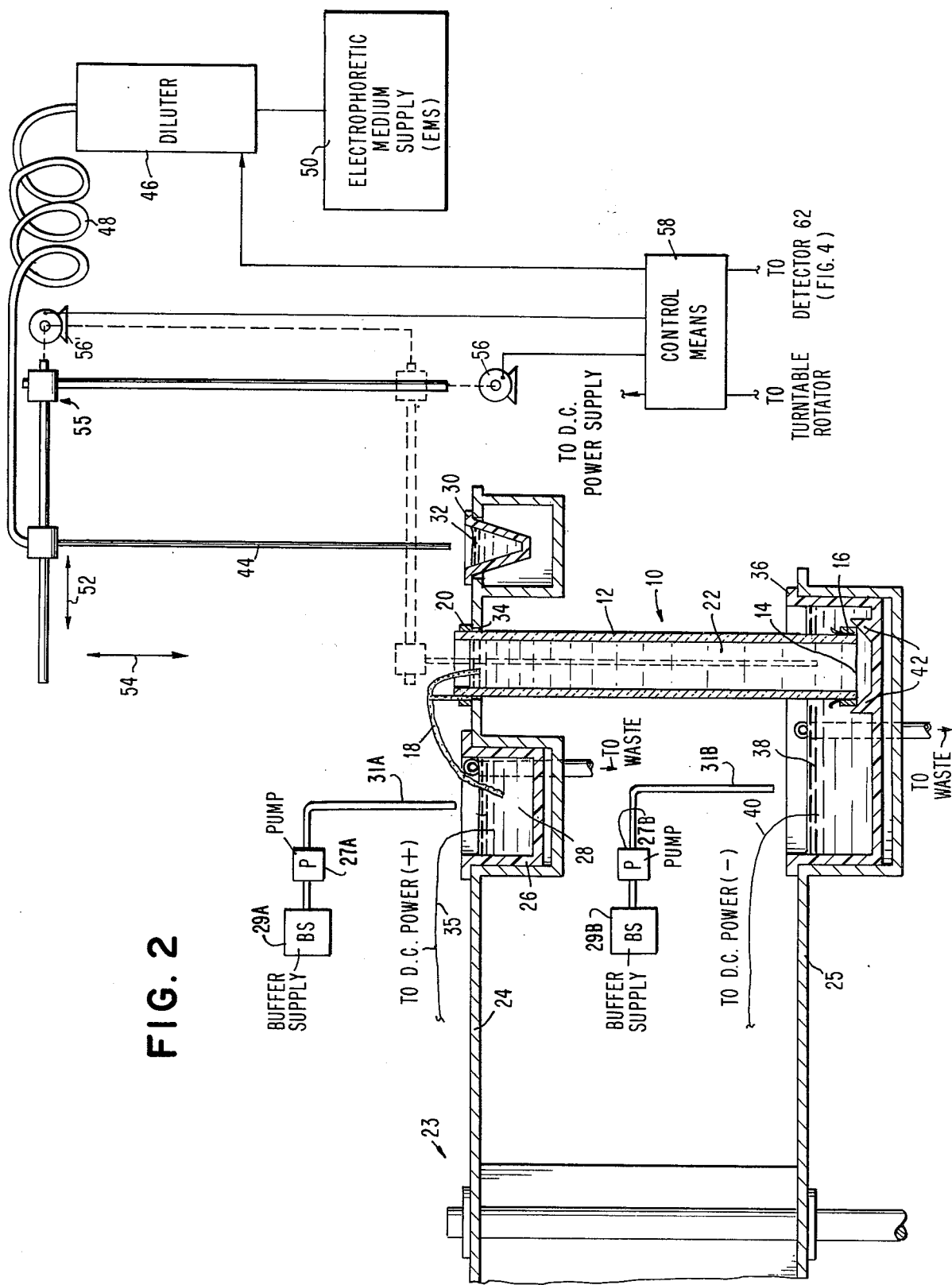
FIG. 2 shows the electrophoresis vessel of FIG. 1 in a system which provides automatic electrophoretic analysis.

FIG. 2 — Automatic Apparatus

This figure shows an automatic electrophoresis apparatus for performing electrophoretic analysis without manual interaction. The electrophoretic vessel 10 fits into a turntable (generally designated 23) having an upper turntable structure 24 and a lower turntable structure 25. Upper turntable structure 24 contains upper buffer container 26 which contains buffer solution 28. The upper structure 24 also includes sample containers 30 which contain samples 32 to be tested, such as blood serum. There is also an opening 34 for loading electrophoretic vessel 10 into the turntable. Conductor 35 makes electrical contact with buffer 28.

The lower turntable structure 25 supports lower buffer container 36, which contains buffer solution 38. A conductor 40 provides electrical contact to solution 38.

The entire turntable structure is cylindrical, having a center at the left of the drawing, as is indicated. Since the turntable structure can be circular and cylindrical, the buffer containers 26 and 36 can be annular structures (for instance, troughs) in the appropriate upper and lower sections 24 and 25. Additionally, the upper buffer containers can be split into two half sections for easier loading. Buffer container 36 may also be provided with guides 42 for vertically locating vessel 10. The buffer solution containers 26 and 36 need not be located in the turntable. For instance, it may be desirable to have lower container 36 be stationary.

As part of an automatic operation which eliminates the need for a technician to fill the buffer containers 26 and 36 daily, it is preferable to utilize a pump 27A to bring the buffer solution from a source 29A to one of the buffer containers, such as the top container 26. The buffer solution flows into container 26 via tubing 31A. Excess buffer solution in container 26 goes to waste.

In a similar manner, pump 27B brings the buffer solution from source 29B to the buffer container 36 via tubing 31B. The excess buffer in container 36 goes to waste. This insures that a fresh buffer solution with the correct pH is always used. As an alternative, a single buffer supply can be used which is connected to a pump which feeds the buffer solution to containers 26 and 36 at the same time. To avoid an electrolytic current path between the buffer containers 26 and 36 during electrophoresis, it would be necessary to have the buffer solution enter the containers as separate droplets (i.e., intermittent flow) rather than in a continuous flow. If desired, the waste buffer solution from container 26 can be intermittently sent to container 36, which will also insure that an adverse current path is not created.

Although a turntable is used for the transport of the electrophoretic vessels, other types of conveyors could also be used. For instance, a linear motion conveyor could be used to take the vessels 10 from the filling station to the detecting station, where the electrophoretic pattern is scanned. The speed of the conveyor is adjusted so that the pattern will be developed sufficiently by the time the vessels arrive at the detector.

The apparatus of FIG. 2 includes a sampler tube 44 which is moveable both horizontally and vertically. Sampler tube 44 is connected to diluter 46 via flexible tubing 48. Diluter 46 is in turn connected to supply 50. Diluters of this type are known in the art. They may be used to pick up a known amount of sample serum, for instance 0.1 ml, which can then be dispensed together with a certain volume of diluent. In the case of electrophoretic analysis, the diluent is an electrophoretic medium.

In FIG. 2, the movement of sampler tube 44 is illustrated by the arrows 52 and 54. In addition, the dashed outlines of this apparatus are shown for use in the discussion of the operation of this apparatus. Movement of the sample tube 44 is conveniently under control of drive means 55 and motor units 56 and 56', which control its vertical and horizontal movements. The total system shown in FIG. 2 can operate under control of a control means 58. Means 58 provides electrical clocking and synchronization signals to the sampler tube motors 56, 56' to the turntable rotator (not shown) used to move the turntable, and to the detector which is shown in more detail in FIG. 4.

FIG. 3

Figure 3:
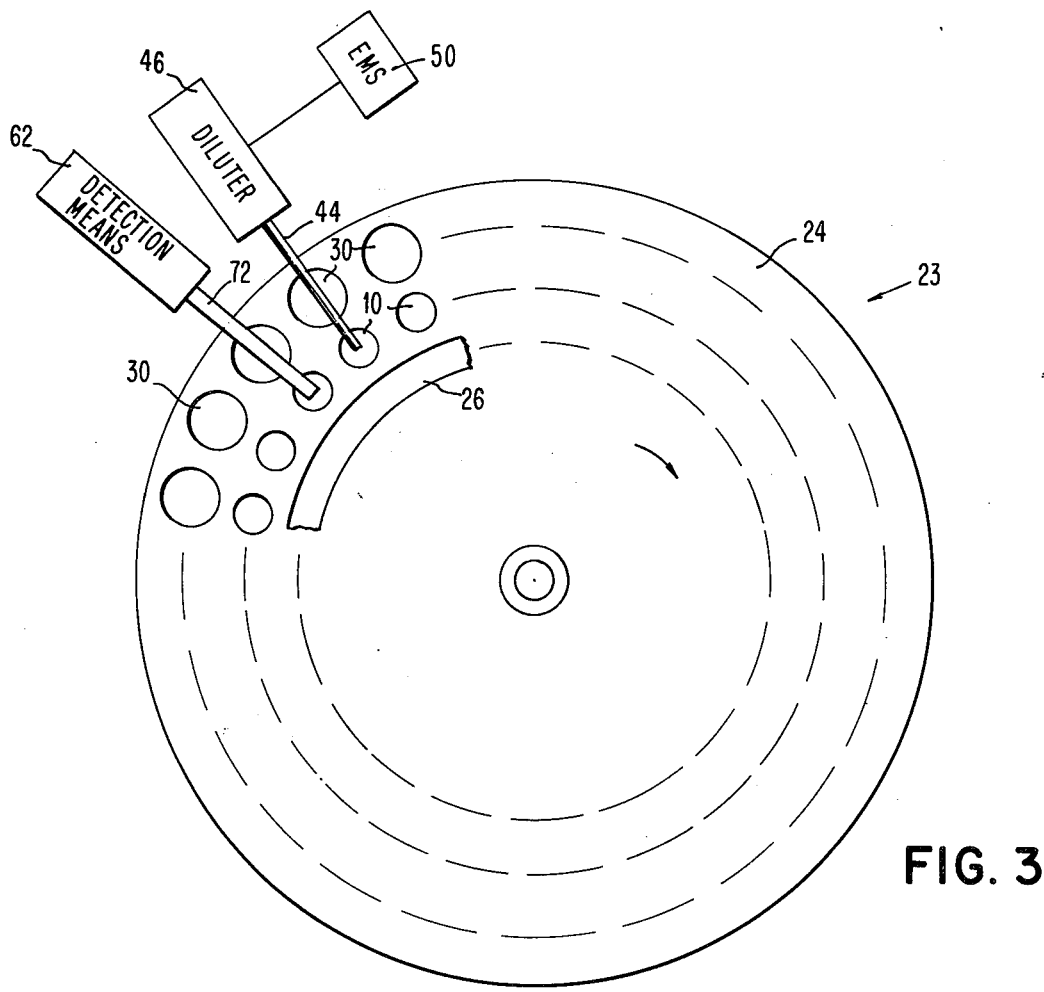
FIG. 3 shows a top view of some of the components shown in FIG. 2, illustrating the positions of the various components with respect to one another.

FIG. 3 is a top view of some of the apparatus shown in FIG. 2. This top view shows the relation between the diluter 46 and the turntable 23 of which top portion 24 is shown. Each hole on the outer ring of portion 24 contains a serum sample container 30 while each hole on the adjacent inner ring contains an electrophoretic vessel 10. The inner, annular trough closer to the center of turntable 23 is the buffer container 26. Also shown is a detector 62 which is shown in more detail in FIG. 4. This detector is used to analyze the electrophoretic patterns produced in the vessel 10.

FIG. 4

This figure shows the scanner/detector 62 which can be moved up and down by turning spindle 64 through motor 66. Detector 62 is provided with light source 68, filter 70, light guide 72 and light guide 74. Light guide 72 emits light only at its lower tip 76 and this emitted light travels to the right due to the angled mirror tip structure 76 of guide 72. The light guides 72 and 74 can be made from, for instance, optical wave guides comprising fiber optic sections.

Light guide 74 receives light only at its lower tip 78, said light coming from the tip 76 of guide 72. Light received by guide 74 is transmitted to light detector 80 which provides signals to utilization means 81. Light source 68 and detector 80 are completely separated by housing 82. Filter 70 is chosen to pass only light of the desired wavelength. This wavelength is selected based on the particular electrophoretic separation to be performed. For instance, for separation and detection of serum proteins a preferred wavelength is about 205 nanometers. A zinc lamp emitting at 213 nm. may also be used. At these wavelengths, proteins absorb strongly with C—N (carbon-nitrogen) bond and may be detected, as is well known. This detection is highly sensitive and accurate. The wavelengths of electromagnetic radiation used for scanning the electrophoretic pattern 75 are known in the art (e.g., about 205 nm., about 280 nm., about 340 nm., or visible light). The wavelength chosen does determine the choice of certain parts of the apparatus. For example, a wavelength of about 210 ± 10 nm. is especially suitable, since all serum protein fractions have about the same absorption coefficient. Of course, an electrophoretic medium which is optically transparent at this wavelength has to be used and light guides 72 and 74 have to be comprised of transparent material, such as good quality quartz. The electrophoretic medium 22 in vessel 10 has to be substantially transparent to the radiation used in the analysis. The buffer compositions which have been described previously are transparent in the wavelength ranges mentioned.

While less preferable, a wavelength range of 280 nm. may also be used for protein detection. For other analysis, preferred optical wavelengths are known in the art. For example, cerebral spinal fluid is scanned at the same wavelengths as are serum proteins. LDH isoenzymes are generally detected at 340 nm., while lipoproteins are scanned according to the dye used in the electrophoretic medium.

Light guides 72 and 74 are thin so that they will not disturb the electrophoretic pattern 75 developed in medium 22 when the guides travel vertically through this medium for scanning of the pattern. A reasonable diameter for these light guides is typically a few millimeters.

Scanning of an electrophoretic pattern while it is within the vessel 10 and by a detector which enters the vessel is extremely useful and economical. For instance, when ultraviolet light (UV) is used, it is difficult to obtain a low cost vessel which would be transparent to UV radiation (for instance, radiation with a wavelength of about 205 nm.). One of the few materials that is transparent to UV light is high purity quartz, which is quite expensive, and therefore cannot be used to make a low cost, disposable vessel 10.

Operation of the Apparatus of FIG. 2

To perform the electrophoretic analysis, the buffer containers 26 and 36 are filled with buffered aqueous solutions which preferably have the same pH, the same ionic strength, or the same composition as electrophoretic medium 22. If an automatic pump is used for supplying buffer to the containers 26 and 36, it is preferable to start the pump before starting the operations so that the old buffer (which may have changed in composition due to aging) is replaced. The serum sample cups 30 are filled with the serums to be analyzed and are inserted into the appropriate openings along the outer perimeter of the turntable platform 24. Empty electrophoretic vessels 10 are inserted in the appropriate inner perimeter openings in the turntable platform 24 and rest on the guides 42 in lower platform 25.

Sampler tube 44 is then dipped into sample cup 30 to pick up a desired known volume of sample 32. This is accomplished by activating the diluter 46 for a pick up cycle. Sample arm 44 is then raised automatically and moved horizontally (in a radial direction) over to the center of electrophoretic vessel 10. Tube 44 is then lowered vertically into vessel 10 until the lower tip of the tube is only a small distance (about 1 mm.) above membrane 12. All horizontal and vertical motions of tube 44 can be carried out by automatic driving mechanisms 56, 56' activated by the control means 58 as illustrated in FIG. 2.

The diluter 46 is then activated to perform its discharge cycle. It slowly discharges (for instance, at the rate of 0.2 ml. per sec.) the serum at the bottom of vessel 10 and then the electrophoretic medium 22. During the discharge, it is preferable that tube 44 be raised at the same rate that vessel 10 is filling, so as not to disturb the layering of the serum at the bottom of vessel 10. The serum sample will flow and stay at the bottom of vessel 10 due to its higher density, and will form a thin, even layer over membrane 14. Electrophoretic medium 22 is discharged over the serum sample and the sampler tube 44 is simultaneously raised so that the discharge of medium 22 does not disturb the serum layer. Medium 22 is filled in this way to the top of vessel 10 until it makes good contact with wick 18. Sampler tube 44 is then returned to its starting position over sample cup 30.

It is desirable that a thin layer of serum sample be formed on the closure membrane 14. This layer is generally less than about 2 mm. in thickness and is spread over the membrane area. Since the serum sample is generally denser than the electrophoretic medium, it can be dispensed into the vessel 10 after medium 22 is dispensed therein. The result is still that the sample serum will form a thin layer at the bottom of vessel 10.

Sampler tube 44 typically enters vessel 10 to a depth which brings it to within a few mm.'s of closure 14. This insures that splashing will be minimal when the dispensing operation from tube 44 begins. Also, the material dispensed (especially the serum sample) will not be appreciably disturbed if the rate of dispensing is sufficiently small, i.e., if the dispensing rate is approximately equal to the rate of movement of tube 44 in vessel 10.

Of course, separate tubes could be used for dispensing the electrophoretic medium 22 and the serum sample, but this would be more costly. Also, the advantage of continual rinsing of the sampler tube after each sample is picked up would be lost if separate dispensing tubes were used.

DC power is then applied between leads 35 and 40 in the polarity indicated in FIG. 2. The DC power may be applied continuously when the apparatus is on. Current will flow only through those vessels which have been filled. That is, electrolytic contact between the wick 18 and the membrane 14 must be established before current will flow. If desired, short power interruptions during each cycle of operation, can be utilized. That is, the positive terminal of the DC power supply (not shown) is attached to lead 35. Typically the applied DC voltage is in the range of about 100-200 volts depending upon the particular dimensions of the apparatus and the ionic strength used. The DC power may be continuously supplied or it may be interrupted.

The turntable is then advanced to its next position so that the next serum sample and the next empty vessel 10 is underneath sampler tube 44. The cycle which was described previously, comprising the picking up of serum and discharging it with the electrophoretic medium is repeated for each sample and each electrophoresis vessel 10.

While the turntable is advancing from position to position, DC power is supplied to each of the filled vessel 10 and the actual electrophoretic operation proceeds in the filled vessel. The turntable can proceed at the rate of, for example, 30 sec. per sample, 1 minute per sample, etc. Since DC power is applied, the electrophoretic separation proceeds and usually after about 20 to 40 minutes of electrophoresis time the electrophoresis pattern may be fully developed. The detector 62 is located with respect to the filling apparatus 44 such that the various sample cups 30 arrive at the position of the detector after about 20 to 40 minutes of electrophoresis time has elapsed. That is, the tubes 10 proceed around the turntable while the DC voltage is applied so that the electrophoresis patterns may be fully developed, when they arrive at the detector 62. The position of the detector may be varied depending on the determinations to be made. Since the control means provides constant times each cycle, the time at which each vessel arrives at the scanning station is the same for each sample.

The preferred starting position of detector 62 is its upper location when it is raised by motor 66 to its uppermost position. Detector 62 is then lowered by motor 66 at a constant speed into vessel 10. After sensor tips 76 and 78 are immersed in medium 22, but have not yet reach the electrophoretic pattern, the background light level is measured. This "background" is the light level without the presence of protein. This light level is automatically held by the detector. Then, the electrophoretic pattern is scanned by advancing detector 62 downwardly at constant speed. The optical density is recorded until the bottom of vessel 10 is reached. The optical signal leaving detector 62 at any time may be processed in the usual way, as known in the electrophoretic art. In practice a utilization means can be employed to receive the outputs of the detector 62. The wavelengths of the radiation used to detect the fractions present is chosen in accordance with the results desired. For instance, electromagnetic energy in the visible, ultraviolet or infrared range may be advantageously used.

A "double scan" may be achieved by detector 62. This type of scan involves recording the electrophoretic pattern when moving downwardly and when moving upwardly in the electrophoretic medium. It will be appreciated that the present method permits an immediate absolute determination of all fractions (e.g., such as albumen and globulin fractions) since the amount of serum is known and the absorbence at the selected wavelength (such as 205 nm.) is known. This is a distinct advantage over present methods of electrophoretic detection which give only relative amounts and which require an additional determination of total protein by an independent method. However, the present apparatus can be used to give the relative amounts of the fractions present, is that is sufficient for the desired analysis.

Determination of LDH Isoenzymes

The detection of isoenzymes has gained wide acceptance in recent years with the recognition that the relative amount of particular electrophoretic fractions is indicative of certain diseases. Such enzymes are detected by their ability to accelerate the rate of specific chemical reactions.

Figure 5:
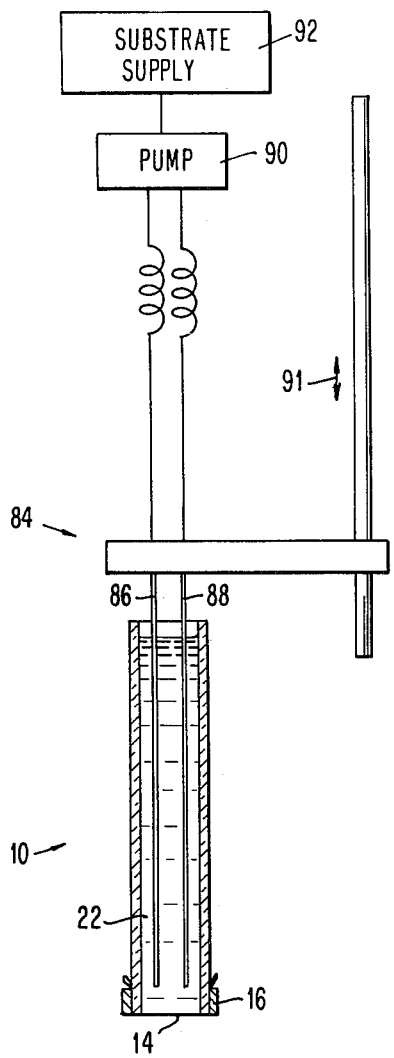
FIGS. 5 and 6 show apparatus particularly suitable for use with the automatic apparatus of FIG. 2, when determination of LDH isoenzymes or alkaline phosphatase isoenzymes is to be performed.
Figure 6:
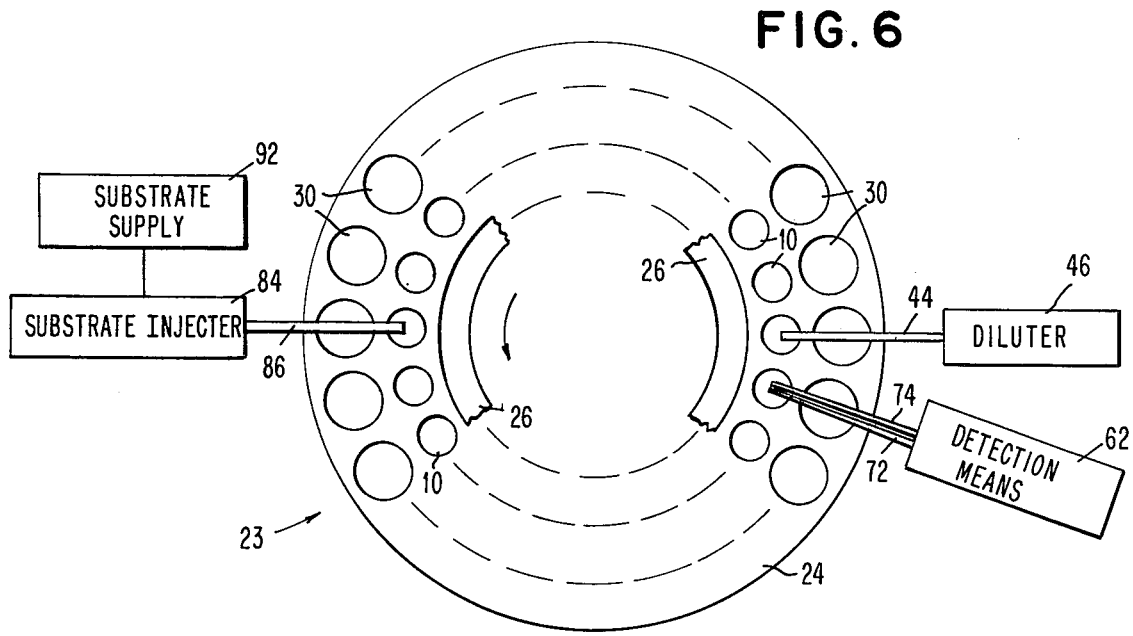

An additional step is required for the determination of these enzymes. The apparatus used for this additional step is shown in FIGS. 5 and 6. In FIG. 5, a substrate injection apparatus is shown, while in FIG. 6 the relative positions of the various pieces of equipment is shown.

In FIG. 5, a substrate injector 84 is used to inject a substrate solution (which will react in the presence of an enzyme) into the electrophoresis vessel 10. This injection occus after the electrophoretic pattern has been developed during the turntable motion of vessel 10 from diluter 46 to substrate injector 84. The substrate solution is pumped into vessel 10 through tubes 86 and 88, by means of a pump 90. The motion (arrow 91) of tubes 86 and 88, and the amount of substrate from substrate supply 92 injected into electrophoretic medium 22 are chosen such that the electrophoretic pattern is not disturbed. The injection is done at a uniform rate, preferably through the whole length of vessel 10.

In order to minimize disturbance of the electrophoretic pattern, it has been found advantageous to inject only in the order of less than 0.1 ml. substrate solution for each ml. of electrophoresis medium. Also, the injection tube diameter should be small, e.g., its diameter should preferably be less than 10% of the total vessel diameter. Furthermore, minimal disturbance of the pattern occurs when tubes 86, 88 are first inserted almost to the bottom of tube 10, without injection of the substrate solution. Injection of this solution is then started at a constant rate and the tubes 86, 88 are withdrawn from vessel 10, simultaneously with injection of the solution.

While it is essential that the electrophoretic pattern is not substantially disturbed by substrate injection, the substrate distribution over the horizontal cross section of vessel 10 may not be even, without affecting the usefulness of the result. It may be advantageous to promote mixing of the substrate and the electrophoretic medium in the horizontal plane, without distorting the pattern along the vertical axis of vessel 10. Such mixing can be promoted by mechanical devices, such as stirrers which are essentially thin and planar. These stirrers can be part of the substrate injection apparatus, or separate therefrom. As an alternative, several injection tubes can be used to distribute the substrate in a horizontal plane. Even if extensive, even distribution is not achieved, the pattern of reacted enzyme and substrate is still useful for determining the relative amounts of the isoenzyme fractions.

The substrates used for developing LDH isoenzymes are well known in the art. For example, the substrate may contain L-lactate and NAD (Nicotin-amide-adenine dinucleotide) which is colorless at 340 nm. The LDH isoenzymes convert this to Pyruvate and NADH which absorbs light at 340 nm. This reaction proceeds while the vessels 10 advance from the location of the substrate injector to the location of the detector, as shown in FIG. 6. The detector, working at 340 nm., will then detect the isoenzyme pattern. For the detection of some isoenzymes, it may be desirable to thermostat the apparatus.

Alkaline phosphatase isoenzymes can be detected by using a reagent, such as p-nitrophenyl phosphate which is colorless at 420 nm. This reagent will react in the presence of the alkaline phosphatase enzyme to produce p-nitrophenoxide which is colored at 420 nm. Thus, the presence of this enzyme can be detected due to this color change at 420 nm.

Lipoproteins may be done by prestaining the serum sample with sudan black or other dyes, as is known in the art. In this case, the serum may be premixed with sudan black before insertion into vessel 10. It should be understood that the injection of a reagent to make an electrophoretic pattern detectable may be applied to electrophoretic patterns other than those of isoenzymes.

By satisfying the general requirement that the reaction of an electrophoretic fraction with a reagent produces or consumes a colored product, the pattern becomes detectable with one of the detectors described herein.

Figure 7:
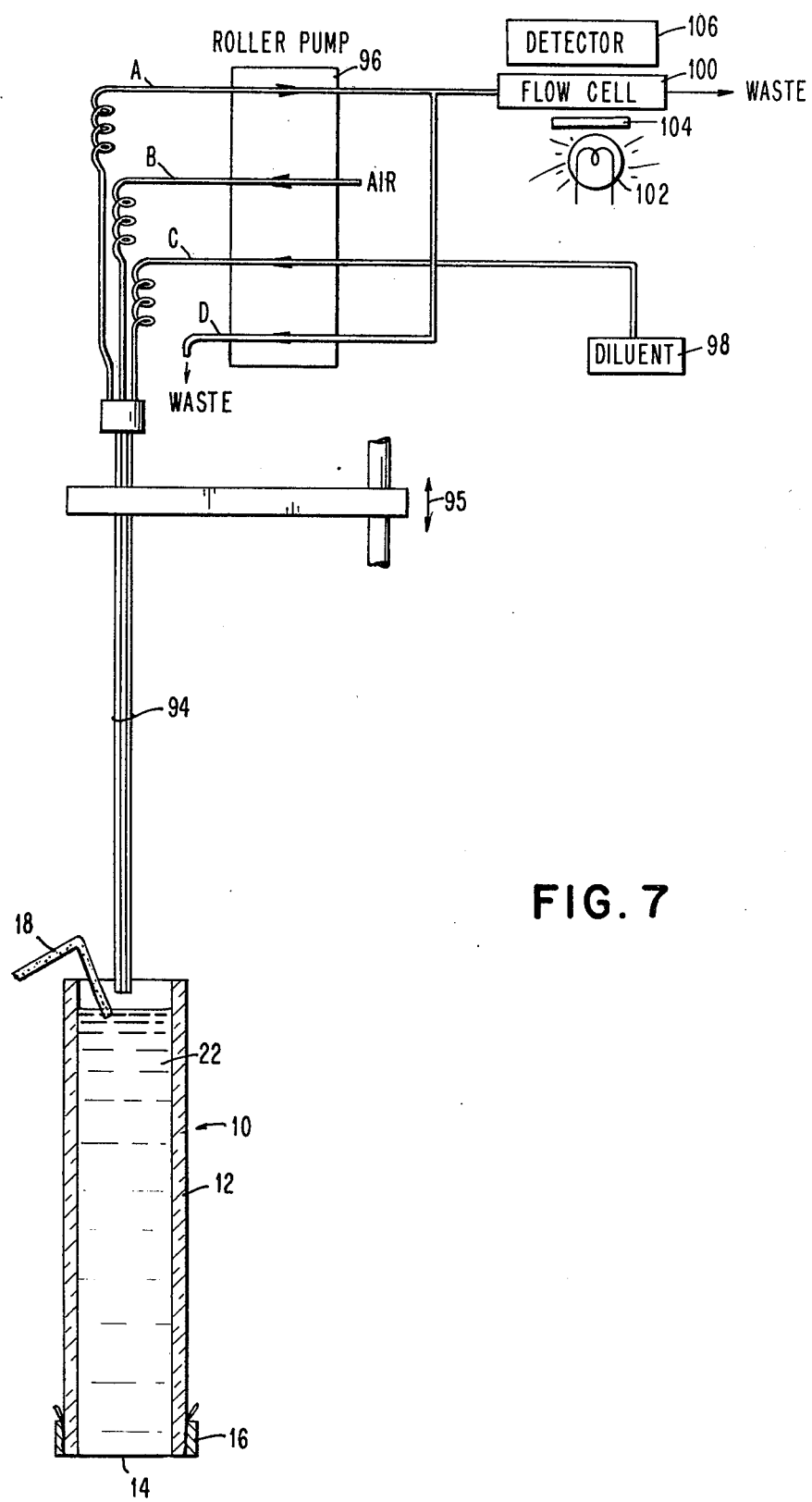
FIG. 7 shows an embodiment of an alternate detection means.

Alternate Detector — FIG. 7

Figure 4:
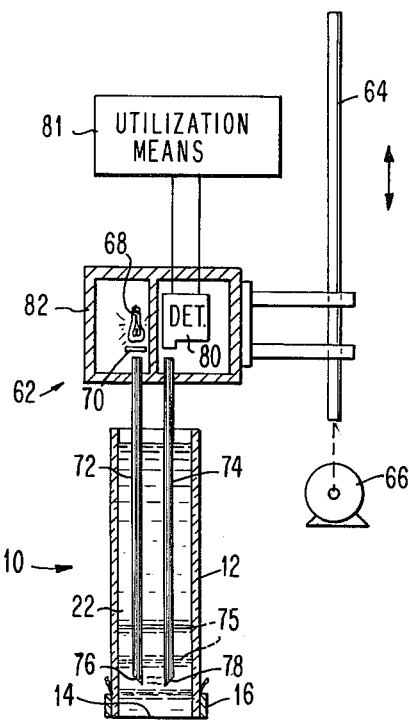
FIG. 4 shows a portion of the system of FIG. 2 and in particular shows the details of a suitable detection means for use in the automatic apparatus of FIG. 2.

FIG. 7 shows an alternate type of detector which may be used in place of the detector 62 shown in FIG. 4. The detector of FIG. 7 is slightly less preferable than detector 62. This alternate detector removes the electrophoretic pattern for detection and measurement outside of vessel 10.

In more detail, arm 94 moves at a preferably constant speed downwardly into electrophoretic vessel 10, being driven in the direction of arrow 95 by a motor (not shown). A pump 96 operates at the same time and can be, for instance, a peristaltic pump. It contains several pump lines A-D which operate at different pump rates. The purpose of this pumping arrangement is to pump representative segments out of the electrophoretic pattern without disturbing the pattern itself, and to segment the sample stream with air. Further, the sample stream is diluted with diluent from supply 98 so that the pattern in the sample stream remains undisturbed until measured in flow cell 100. To achieve this, the pump rate in line A is slightly higher than the sum of the pump rates in lines B and C, the difference A-(B+C) being the pump rate at which electrophoretic medium 22 is pumped upwardly. It is preferable that the rate of buffered pumping of the electrophoretic medium 22 is such that only a fraction of the contents of vessel 10 is pumped while arm 94 is moved downwardly. This insures that the electrophoretic pattern in vessel 10 remains undisturbed.

While air segmentation of the sample stream and dilution are preferably carried out directly at the lower tip of arm 94, these operations may also be carried out further downstream. While less preferable, this apparatus will work without dilution of the sample stream. Also, pump line D is used to debubble the stream before it reaches flow cell 100. Modern techniques do not require debubbling before measuring the sample stream and, of course, these new techniques may also be employed herein.

The light absorption in the sample stream is measured in flow cell 100 by means of light source 102, filter 104, and detector 106, as is known in the art. The signal from detector 106 may then be processed in a conventional manner.

Density Gradient Electrphoresis — FIGS. 8-10

These figures relate to an apparatus and technique for density gradient electrophoresis. This type of electrophoresis is well known and has been described in numerous journals, as for example, F. W. Sunderman et al, American Journal of Clinical Pathology, Vol. 45 pages 381-397 (1966), and L. T. Skeggs et al, Annual of the New York Academy of Science, Vol. 102, pages 144-160 (1962).

Density gradients are often formed using aqueous solutions of sucrose, although other types of heavy solutions can also be used. Higher sucrose concentrations yield higher densities, i.e., higher weight per ml. FIG. 8 shows the presence of a density gradient in the electrophoretic vessel 10. The lines in the electrophoretic medium 22 are indicative of the densities along the length L of vessel 10.

In FIG. 9, the percentage of sucrose in an aqueous solution is plotted along the horizontal axis while the length L of vessel 10 is plotted along the vertical axis. This plot therefore shows the distribution of the sucrose concentration in vessel 10.

The bottom of tube 10 contains the heaviest solution, with gradually lighter solutions layered toward the top of the vessel. Near the bottom of vessel 10 there is provided a sharp change in sucrose concentration, noted as a "shelf" for the sample. The sample, which can be serum, has a density which is lower than that of the "shelf", but higher than that of the higher solution layers. Therefore, the serum will sit as a well defined layer on the shelf. The advantage of such density gradient electrophoresis is mainly that, by having layers of decreasing density toward the top of the vessel, the layers do not mix due to small mechanical or normal disturbances. Therefore the electrophoretic pattern is stabilized.

FIG. 10 schematically illustrates the preparation of variable density gradients in the electrophoretic vessel 10. Pumps 108A and 108B are variable rae pumps. Firstly, pump 108A is run at a higher speed than pump 108B to make a solution of high density. Then, pump 108A is gradually slowed and pump 108B speeds up until vessel 10 is filled. The nozzle 110 which delivers the mixed solution to the vessel 10 may be raised (arrow 111) as the vessel is filling to avoid undesired mixing in vessel 10. Apparatus to achieve the raising of nozzle 110 is well known in the art, as is apparatus for producing density gradients.

Pump 108A receives a sucrose solution and a buffer from supply 112A, while pump 108B receives water and a buffer from supply 112B.

The density gradient electrophoresis technique may be used in the apparatus previously described in this patent application. The electrophoretic vessel 10 of FIG. 1 is inserted into the turntable in the usual manner. It is then filled with electrophoretic medium 22 containing the density gradient. After this it proceeds to diluter 46 where the serum sample is inserted onto the "shelf" with arm 44 (FIG. 2). Arm 44 is lowered to the location of the shelf before the serum sample is inserted. Diluter 46 does not deliver any substantial amounts of the electrophoretic medium in the manner described earlier. Instead, diluter 46 discharges some solution from supply 50 (FIG. 2) into waste in order to be clean for the next sample. All other operations are similar to those described earlier. Detection of the electrophoretic pattern is again carried out with the devices shown in FIGS. 4 and 7. A suitable wavelength for scanning is about 280 nm. Other types of detection, such as those using chemical reagents, may also be used. Analysis of species such as hemoglobin, lipoproteins, LDH isoenzymes, may also be achieved as described previously. It is understood that, while UV detection is most preferable, visible light detection may also be used when serum is prestained, as is known in the art. Further, the gradient shelf may be used to raise the position of the serum sample higher (i.e., away from membrane 14) with some advantage, even without generating a density gradient over the whole tube length.

What has been described is an apparatus and a method for the completely automatic electrophoresis of various samples. This analysis provides fast and accurate determinations without requiring operator time. Certain parts of this system, such as the optical detector (FIG. 4), the vessel 10, and the vessel filling apparatus, may be employed advantageously in other systems, or even by themselves, as will be appreciated by those having skill in these arts.

I claim:

1. A method for analyzing a sample by zone electrophoresis, comprising the steps of:
   moving a vessel by a conveyor means to a first position,
   filling said vessel at said first position with said sample to be analyzed and with an electrophoretic medium,
   moving said vessel to a second position,
   passing an electrolytic current through said vessel, said sample, and said medium at a time when said vessel has moved from said first position toward said second position to establish in said medium an electrophoretic zone pattern comprised of separated thin layers of constituents of said sample,
   detecting said zone pattern while it is in said electrophoretic medium when said vessel is at said second position to analyze said sample.

2. The method of claim 1, where said detecting step comprises scanning said pattern with electromagnetic energy which does not pass through said vessel during said scanning.

3. A method for zone electrophoresis of a sample, comprising the steps of:
   moving a vessel by a conveyor means to a first position,
   placing a thin layer of said sample into said vessel, followed by placement of an electrophoretic medium on said sample, said electrohoretic medium being capable when loaded onto said sample of immediate electrophoretic operation,
   moving said vessel to a second position,
   passing an electrolytic current through said vessel, said sample, and said electrophoretic medium during the time period of movement of said vessel to said second position to establish an electrophoretic zone pattern comprised of separated thin layers of constituents of said sample, and
   detecting said zone pattern when said vessel is at said second position to analyze said sample.

4. The method of claim 3, wherein said detecting step comprises removing said sample from said vessel without substantially disturbing said pattern, and then scanning said pattern to determine the constituents of said sample.

5. The method of claim 1, including the further step of adding a reagent to said vessel after said pattern is developed and prior to said detecting step to determine the presence of isoenzymes in said sample.

6. The method of claim 1, including the further step of adding a reagent to said vessel before said electrolytic current is passed through said medium and sample to determine the presence of lipoproteins in said sample.

7. The method of claim 4, where the volume of said reagent is less than about 10% of the volume of said electrophoretic medium.

8. The method of claim 1, including the step of establishing an electrophoretic medium of variable density in said vessel.

9. A method for electrophoretic analysis of samples, comprising the steps of:
   filling a vessel with a sample to be analyzed, then filling said vessel with an electrophoretic medium,
   establishing an electric field in said vessel to produce an electrophoretic pattern therein characteristic of said sample,
   optically scanning said pattern with an optical beam to determine the constituents of said sample, said optical beam being wholly within said vessel.

10. The method of claim 9, including the further step of injecting a substrate solution into said vessel after said pattern is established.

11. The method of claim 3, where said detecting step occurs while said zone pattern is in said electrophoretic medium.

12. The method of claim 3, wherein said vessel is filled with said sample and said electrophoretic medium by the following steps:
   moving the tip of a sample tube having said electrophoretic medium therein into said sample,
   filling the tip of said sample tube with said sample by drawing said sample into said tip,
   removing said sample tube from said sample,
   moving said sample tube into said vessel, and
   dispensing said sample and then said electrophoretic medium from said sample tube into said vessel.

13. An apparatus for electrophoretic analysis of samples, comprising:
   a plurality of tubular vessels into which said samples and an electrophoretic medium can be placed, each said vessel having a closure at one portion thereof through which an electrolytic current can pass,
   a turntable which can support said vessels for movement of said vessels from a filling station to a detecting station,
   a filling station including means for placing thin layers of said samples into said vessels and for placing a flowable electrophoretic medium into said vessels, said filling station including a supply of said electrophoretic medium,
   an electric means for producing an electrophoretic pattern characteristic of said sample in said vessel during the time period while said vessel is being moved by said turntable from said filling station to said detecting station,
   a detection station for scanning said electrophoretic pattern with an optical beam which does not intersect said vessel during said scanning operation.

14. The apparatus of claim 13, where said electric means includes buffer containers for containing buffer solutions which make electrolytic contact with said sample and said electrophoretic medium in said vessels.

15. The apparatus of claim 14, further including pump means for pumping said buffer solution into said containers.

16. The apparatus of claim 15, further including a control means for activating the operation of said filling station, said detection station, and said pump means, said pump means being activated prior to the operation of said electric means.

17. The apparatus of claim 13, further including an injection means for placing a substrate solution into said vessel after said electrophoretic pattern is produced and prior to the time when said scanning occurs, for detection of isoenzymes in said sample.

18. An apparatus for zone electrophoretic analysis of a sample, comprising:
   a tubular vessel for containing an electrophoretic medium and a sample which is to be electrophoretically analyzed,
   a sample container for containing said sample, a supply for containing an electrophoretic medium which can flow, transfer means for transferring said sample from said sample container to said vessel, and for transferring said electrophoretic medium from said supply for injection into said vessel, electric means for providing a voltage in said electrophoretic medium and said sample in said vessel to establish an electrophoretic zone pattern therein comprised of thin layers of fractions from said sample, and detection means for optically scanning said electrophoretic zone pattern while said fractions are in said electrophoretic medium, a conveyor for supporting said vessel and said sample container, and for transporting said vessel from said transfer means to said detection means, said electrophoretic pattern being established during a portion of the time period taken by the conveyor to move said vessel to said detection means.

19. The apparatus of claim 18, including control means for sequencing the operation of said transfer means, said detection means and said conveyor.

20. The apparatus of claim 18, where said transfer means and said detection means are located in different positions about the periphery of said conveyor.

21. The apparatus of claim 18, where said detection means includes a source of electromagnetic energy and guides for said electromagnetic energy, and further means for inserting said guides into said electrophoretic medium.

22. The apparatus of claim 18, further including buffer containers for containing buffer solutions for making electrolytic contact with said electrophoretic medium and said sample.

23. The apparatus of claim 22, where said vessel is tubular and has a membrane at one end thereof, said vessel being supported so that said membrane makes electrolytic contact with said buffer solution.

24. The apparatus of claim 18, where said conveyor is a turntable.

25. An apparatus for electrophoretic analysis of samples, comprising:

a plurality of vessels adapted to be carried by a support means, a support means for moving said vessels along a predetermined path of movement, dispensing means for dispensing an electrophoretic medium and samples into said vessels, said dispensing means being located in a first position along said path of movement followed by said vessels, electric means for establishing an electrophoretic pattern in said vessels while said vessels are moved along said path, detection means for sensing said pattern, said detection means being located in a second position along said path sufficiently removed from said first position that said electrophoretic pattern is developed in said vessels by the time said vessels reach said second position, control means for sequencing the operation of said insertion means, and said detection means.

26. The apparatus of claim 25, wherein said electrophoretic medium in said vessels has a density gradient as measured along a direction defined by the electrophoretic pattern.

27. The apparatus of claim 26, further including means for establishing said density gradient of electrophoretic medium in said vessels.

28. The apparatus of claim 27, where said vessels are tubular, and said dispensing means includes a tubular member which is movable into and out of said vessel, said tubular member being connected to a diluter which is supplied with said electrophoretic medium.

29. The apparatus of claim 25, where said detection means includes scanning means insertable into said vessel for scanning said electrophoretic pattern therein.

30. The apparatus of claim 29, where said scanning means is comprised of light guides sufficiently small to be inserted into said vessel without substantially disturbing said electrophoretic pattern therein.

31. The apparatus of claim 25, where said samples exist as thin layers having a thickness less than about 2 mm., in said vessels.

32. An apparatus for detection of an electrophoretic pattern established in a vessel containing an electrophoretic medium and a sample to be analyzed, comprising:

a source of electromagnetic energy, guide means for guiding said electromagnetic energy, means for moving said guide means into and out of said electrophoretic medium to scan said pattern with said electromagnetic energy, and detector means for measuring said scanned pattern.

33. An apparatus for detection of an electrophoretic pattern established in a vessel containing an electrophoretic medium and a sample to be analyzed, comprising:

a source of electromagnetic energy, transmitting means for transmitting a beam of said energy, receiving means for receiving said energy from said transmitting means, means for placing said transmitting means and said receiving means into said vessel and for removing said transmitting means and said receiving means from said vessel, detector means connected to said receiving means for measuring said pattern, said energy being passed from said transmitting means to said receiving means through said pattern.

34. The apparatus of claim 33 including means to activate said electromagnetic source during the movement of said transmitting means and said receiving means in said vessel.

35. The apparatus of claim 33, where said transmitting means and said receiving means enter electrophoretic medium and are sufficiently small that they do not substantially disturb said pattern.

36. The apparatus of claim 33, where said transmitting means and said receiving means move at constant speed in said vessel.

37. An apparatus for electrophoretic analysis of samples, comprising:

a tubular shaped vessel having a closure at one end thereof through which an electrolytic current can pass, said vessel containing a thin layer of said sample and an electrophoretic medium, a conveyor for supporting said vessel and for transporting said vessel to a detection means, electric means for producing an electrophoretic pattern in said vessel which is characteristic of said sample, said electric means being operative to produce said pattern during the time said vessel is being transported to said detection means, and detection means for scanning said pattern with a light beam, said detection means including light guides which pass through said electrphoretic medium for guiding said light beam across said pattern, thereby scanning said pattern.

38. The apparatus of claim 37, where said light beam does not intersect said vessel during said scanning, said light beam having a width less than about 2 mm.

39. An apparatus for zone electrophoretic analysis of a sample, comprising:
- a vessel for containing an electrophoretic medium and a sample which is to be electrophoretically analyzed,
- a sample container for containing a sample which can flow,
- a supply for containing said electrophoretic medium which can flow,
- transfer means for transferring said sample from said sample container to said vessel, and for transferring said electrophoretic medium from said supply to said vessel, said transfer means including injection means for injecting said sample into the said vessel and for injecting said electrophoretic medium over said sample, said electrophoretic medium being capable of electrophoretic operation immediately after being loaded into said vessel,
- electric means for providing a voltage in said electrophoretic medium and said sample in said vessel to establish an electrophoretic zone pattern therein comprised of thin layers of constituents in said sample,
- detection means for scanning said electrophoretic zone pattern,
- a conveyor for supporting said vessel and said sample container, and for transporting said vessel from said transfer means to said detection means during a time period in which said electrophoretic pattern is established.

40. The apparatus of claim 39, where said detection means includes means for removing said electrophoretic medium and said sample from said vessel after said electrophoretic pattern is established therein, without substantially disturbing said pattern.

41. The apparatus of claim 39, wherein said transfer means includes means for loading said sample into said vessel prior to loading said electrophoretic medium into said vessel.

42. An apparatus for zone electrophoretic analysis of a sample, comprising:
- a vessel for containing an electrophoretic medium and a sample which is to be electrophoretically analyzed,
- input means for putting said sample and said electrophoretic medium in said vessel when said vessel is at a first position,
- electric means for providing a voltage in said electrophoretic medium and said sample in said vessel to establish an electrophoretic zone pattern therein comprised of thin layers of fractions from said sample,
- detection means for scanning said electrophoretic zone pattern when said vessel is at a second position, and
- conveyor means for transporting said vessel from said first position to said second position while said electrophoretic zone pattern is developing in said vessel.

43. The apparatus of claim 42, where said input means includes means for putting said sample into said vessel and then putting said electrophoretic medium into said vessel.

* * * * *